United States Patent
Joosten

(10) Patent No.: US 7,227,636 B2
(45) Date of Patent: Jun. 5, 2007

(54) APPARATUS AND METHOD FOR THE SPECTROSCOPIC DETERMINATION OF CARBON

(75) Inventor: Heinz-Gerd Joosten, Kranenburg (DE)

(73) Assignee: Spectro Analytical Instruments GmbH & Co. KG (DE)

( * ) Notice: Subject to any disclaimer, the term of this patent is extended or adjusted under 35 U.S.C. 154(b) by 41 days.

(21) Appl. No.: 11/139,735

(22) Filed: May 27, 2005

(65) Prior Publication Data

US 2006/0023210 A1   Feb. 2, 2006

(30) Foreign Application Priority Data

Aug. 2, 2004   (DE) ...................... 10 2004 037 623

(51) Int. Cl.
*G01J 3/443*   (2006.01)
*G01N 21/67*   (2006.01)

(52) U.S. Cl. ..................................... 356/313

(58) Field of Classification Search ................. 356/313
See application file for complete search history.

(56) References Cited

U.S. PATENT DOCUMENTS 3,367,229 A   2/1968   Berneron

FOREIGN PATENT DOCUMENTS

| DE | 1 104 736 | 3/1959 |
|---|---|---|
| DE | 341 809 | 2/1978 |
| DE | 197 50 133 | 7/1990 |
| DE | 39 16 833 | 11/1990 |
| DE | 101 25 415 | 11/2002 |
| JP | 10-281996 | * 10/1998 |

OTHER PUBLICATIONS

Article, P.A. 416727★-3.7.61 "Spectrographische . . . Stählen" (Török & Szikora).
Article, Phillips, "Luft- . . . PV 8250".

* cited by examiner

*Primary Examiner*—F. L. Evans
(74) *Attorney, Agent, or Firm*—Robert W Becker & Associates; Robert W Becker

(57) ABSTRACT

An optical emission spectrometer for analysis, identification or identity testing of metallic materials, and a method for optical emission analysis of metallic materials with a spectrometer, wherein the spectrometer has at least one arc or spark generator for producing a discharge between an electrode and a workpiece in a spark stand chamber of the generator. A cleansing apparatus for air about the discharge includes a pump for feeding air into the spark stand chamber, and a container through which air can flow. The container contains an alkaline metal or alkaline earth metal hydroxide or another substance that binds $CO_2$ present in air.

8 Claims, 2 Drawing Sheets

APPARATUS AND METHOD FOR THE SPECTROSCOPIC DETERMINATION OF CARBON

BACKGROUND OF THE INVENTION

The present invention relates to an apparatus in the form of an optical emission spectrometer for the analysis, identification or identity testing of metallic materials. The present invention also relates to a method for the optical emission analysis of metallic materials with a spectrometer having at least one arc or spark generator, the spark stand chamber of which is flushed with air.

Spectrometers in general are used for example for the identification of steels. Steels of different compositions cannot be distinguished from one another outwardly. This means that confusion of different materials can arise at any point between production and processing. In the past such confusion has resulted in considerable economic losses. Precautions are therefore needed in the steel-making and processing industries to avoid confusion between materials. Identity testing instruments are used for outgoing products leaving the steelmaker and for incoming products prior to processing in order to verify that the steel is of the expected grade.

The following types of instruments are used for identity testing:
1. Optical emission spectrometers with electric spark discharge in an argon atmosphere (spark OES)
2. Optical emission spectrometers with electric arc discharge in air (arc OES)
3. Energy-dispersive X-ray fluorescence spectrometers (XRF).

The principle of measurement underlying spark OES and arc OES is for example by Kipsch (Dieter Kipsch, Lichtemissionsspektrometrie, VEB Deutscher Verlag für Grundstoffindustrie, Leipzig, 1974) and Thomsen (Volker B. E. Thomsen, Modern Spectrochemical Analysis of Metals), ASM International, 1996). Information about energy-dispersive X-ray fluorescence spectrometers is provided by Otto (Matthias Otto, Analytische Chemie, Wiley-VCH, Weinheim, N.Y., 2000).

With all three types of instruments, a probe is placed on the workpiece for which the determination is to be made, in other words, measurement is possible without removing a sample.

Spark OES instruments are relatively large (weighing about 25 kg) and additionally require a pressurized gas cylinder of about the same weight containing argon for the discharge atmosphere. A single measurement usually takes longer than 10 s. Before measurement, a flat surface has to be created by grinding the material that is to be tested.

XRF instruments are small and light (weighing less than 2 kg). A single measurement takes about 5 s. Little is required by way of sample preparation. Grinding is usually unnecessary.

However, only elements present in amounts of more than 0.5% can be reliably determined with X-ray fluorescence. These systems cannot be used to determine the light elements C, P, S and Mg in an iron base.

Arc OES instruments are available as small and lightweight systems. Measurements can often be made without having to grind the workpiece. Single measurement times of 3 s are usual.

Most relevant elements can be determined with sufficient accuracy.

Many chemical elements can be identified and quantitatively determined with arc spectrometers.

However, carbon cannot be determined with the necessary accuracy because atmospheric carbon dioxide gives a strong background signal. The $CO_2$ content of ambient air (normally 360 ppm) results in a carbon signal on the carbon line at 193.0 nm which corresponds to the signal for a content of about 0.25% C in steels.

However, carbon in particular has a significant influence on the physical properties of metallic materials, such as steel.

It is therefore an object of the present invention to provide an apparatus and a method for improved C determination.

SUMMARY OF THE INVENTION

This object is achieved by an apparatus having at least one arc or spark generator that produces a discharge between an electrode and a workpiece in the spark stand generator, wherein a cleansing apparatus, for air about the discharge, includes a pump for feeding air into the spark stand chamber, and a container disposed upstream of the spark stand chamber through which air can flow, with the container containing an alkali metal or alkaline earth metal hydroxide or another substance that binds $CO_2$ present in air. By supplementing an arc OES system with an apparatus that enables the electric arc to burn in an atmosphere from which carbon dioxide has been at least almost completely removed, there can be provided lightweight, highly-portable and reasonably priced identity testers that make it possible to test steel grades that are characterized by only small differences in their carbon content.

BRIEF DESCRIPTION OF THE DRAWINGS

Two embodiments are described herebelow with reference to the drawings, in which.

DESCRIPTION OF SPECIFIC EMBODIMENTS

Figure 1:
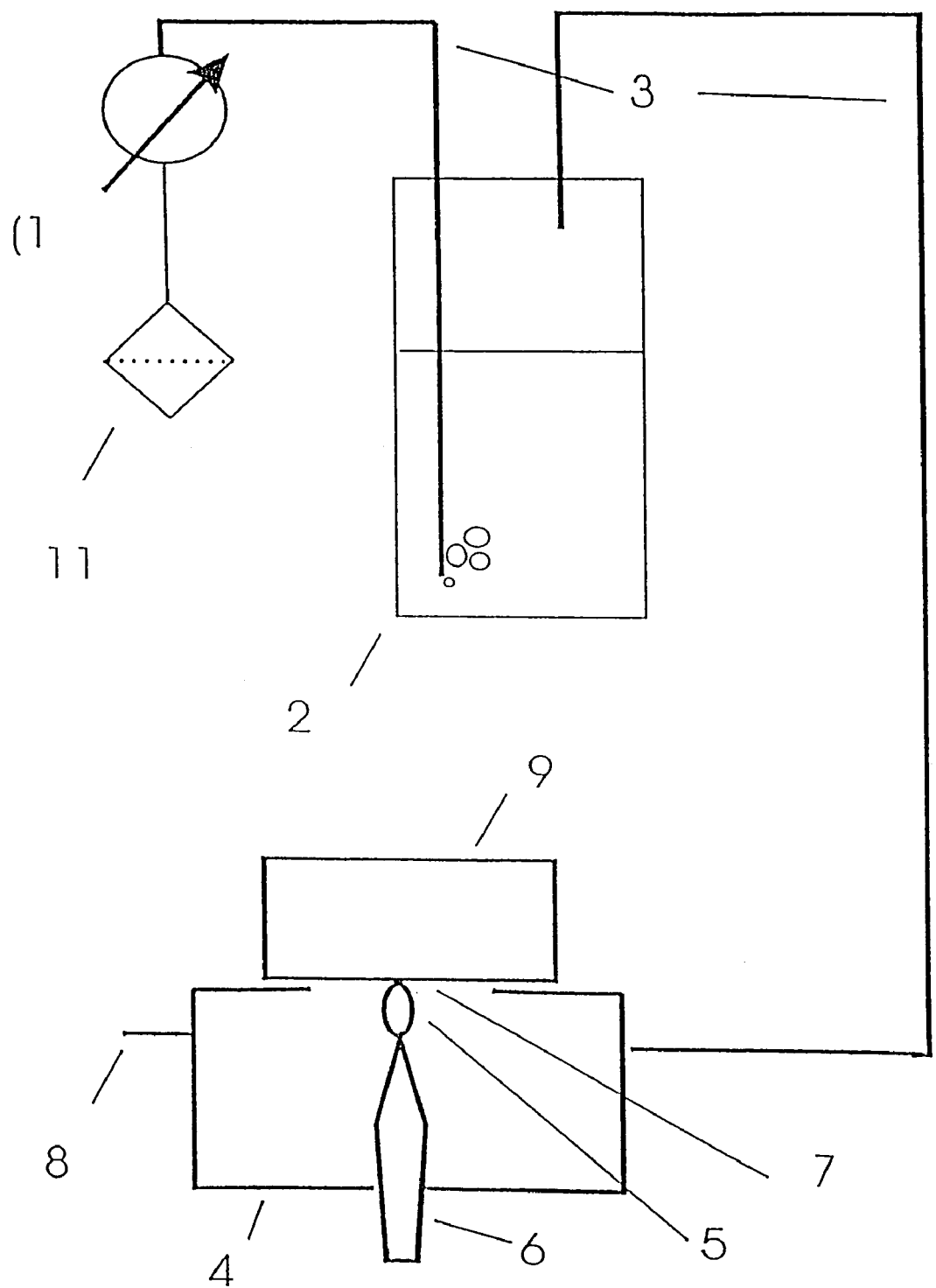
FIG. 1 shows an apparatus for carbon analysis with $CO_2$ absorption in aqueous solution.

FIG. 1 shows diagrammatically an apparatus in accordance with the invention in which air is cleansed of $CO_2$ by means of an aqueous solution.

A diaphragm pump 1 draws ambient air through a particle filter 11 and conveys it through a wash bottle or bubbler 2 containing an aqueous solution of an alkali metal or alkaline earth metal hydroxide, for example $Ca(OH)_2$. The $CO_2$ present in the air reacts as follows:

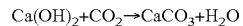

$$Ca(OH)_2 + CO_2 \rightarrow CaCO_3 + H_2O$$

The air, now substantially free of $CO_2$, is conveyed through PTFE tubing 3 to a spark stand chamber 4 of a probe which separates an arc 5 burning between a counter-electrode 6 and a workpiece surface 7 from the ambient air. Exhaust tubing 8 prevents $CO_2$ penetration resulting from turbulence or back-diffusion. The volume of the spark stand chamber 4 can thus be flushed with air that is virtually $CO_2$-free.

The method in accordance with the invention is carried out in the following manner:

First, the probe is placed on the workpiece 9, thereby substantially isolating the spark stand chamber 4 from the outside atmosphere. The $CO_2$-containing air inside the spark stand chamber 4 is then replaced with cleansed air at a flushing rate of about 2 l/min.

After about 0.5 s, the spark stand chamber 4 is filled with cleansed air and the flushing rate is reduced for example to 0.5 l/min by reducing the diaphragm pump supply voltage. This prevents arc blowing. The arc can now be struck without the risk of contamination with $CO_2$.

Figure 2:
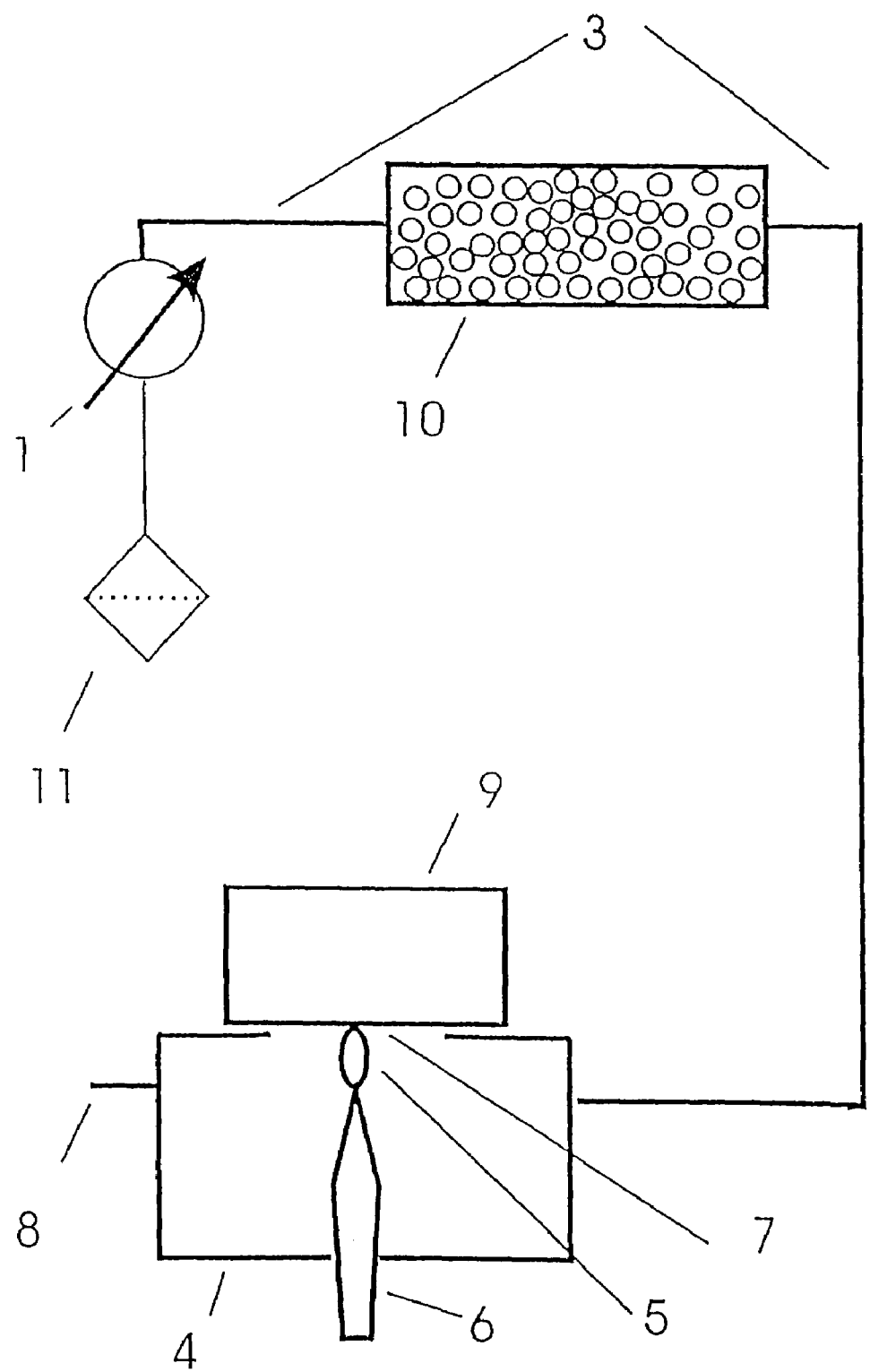
FIG. 2 shows an apparatus according to FIG. 1 with absorption in a solids bed.

The use of concentrated aqueous hydroxide solutions is a problem with portable measuring systems for safety reasons. In the apparatus shown in FIG. 2, cleansing can also be carried out with a bed of solid hydroxide. FIG. 2 shows the corresponding arrangement. The diaphragm pump 1 conveys the ambient air into a sealed container containing a bed 10 of NaOH or $Ca(OH)_2$. These highly hygroscopic substances can be prevented from deliquescing or liquifying by applying the hydroxide to a substrate.

The above-described method can also be used with spectrometer systems in which the excitation source is an electric spark discharge in air.

The specification incorporates by reference the disclosure of German priority document 10 2004 037 623.9 filed Aug. 2, 2004.

The present invention is, of course, in no way restricted to the specific disclosure of the specification and drawings, but also encompasses any modifications within the scope of the appended claims.

The invention claimed is:

1. An optical emission spectrometer for the analysis, identification or identity testing of metallic materials, comprising:
    at least one arc or spark generator having a spark stand chamber, wherein said generator produces a discharge between an electrode and a workpiece in said spark stand chamber; and
    a cleansing apparatus for air about said discharge, wherein said cleansing apparatus inclues a pump for feeding air into said spark stand chamber, and a container disposed upstream of said spark stand chamber, wherein air is adapted to flow through said container, and wherein said container contains an alkali metal or alkaline earth metal hydroxide or another substance that binds $CO_2$ present in air.

2. A spectrometer according to claim 1, wherein said container comprises a washing device having an aqueous solution of an alkali metal or alkaline earth metal hydroxide or any other liquid that binds $CO_2$ present in air.

3. A spectrometer according to claim 1, wherein said container comprises a washing device having a solid bed of an alkali metal or alkaline earth metal hydroxide or any other substance that binds $CO_2$ present in air.

4. A spectrometer according to claim 1, wherein said pump is a diaphragm pump that can be operated with at least two rates of delivery.

5. A method for optical emission analysis of metallic materials, including the steps of:
    providing a spectrometer having at least one arc or spark generator having a spark stand chamber;
    passing ambient air through a container that contains a substance that absorbs $CO_2$ present in the air that is to be cleansed to produce $CO_2$— depleted air;
    passing the $CO_2$-depleted air into the spark stand chamber, which excludes ambient air;
    generating an arc or spark discharge in the spark stand chamber; and
    analyzing the spectrum of the discharge to aid in the identification or identify testing of metallic materials.

6. A method according to claim 5, wherein the container is filled with a bed of a hydroxide of an alkali metal or of an alkaline earth metal or any other solid material that binds $CO_2$ present in air.

7. A method according to claim 5, wherein the container comprises a washing device having an aqueous solution of an alkali metal or alkaline earth metal hydroxide or any other liquid that binds $CO_2$ present in air.

8. A method according to claim 5, which includes the further step of providing a diaphragm pump for conveying cleansed air into the spark stand chamber, wherein the diaphragm pump initially conveys cleansed air into the spark stand chamber at a first flow rate before the arc or spark is generated, wherein the diaphragm pump is then switched to a second flow rate immediately prior to or after the arc or spark has been struck, and wherein the first flow rate is greater than the second flow rate.

* * * * *